US008515837B2

(12) United States Patent
Kudoh et al.

(10) Patent No.: US 8,515,837 B2
(45) Date of Patent: Aug. 20, 2013

(54) METHOD OF BOXING FUEL INJECTORS

(75) Inventors: Tetsuji Kudoh, Kariya (JP); Takanobu Aochi, Nishio (JP); Hisatoshi Tsukahara, Okazaki (JP)

(73) Assignee: Denso Corporation, Kariya (JP)

( * ) Notice: Subject to any disclaimer, the term of this patent is extended or adjusted under 35 U.S.C. 154(b) by 1253 days.

(21) Appl. No.: 12/076,188

(22) Filed: Mar. 14, 2008

(65) Prior Publication Data

US 2008/0235117 A1 Sep. 25, 2008

(30) Foreign Application Priority Data

Mar. 23, 2007 (JP) ................. 2007-076919

(51) Int. Cl.
*G06Q 10/00* (2012.01)
*A01K 5/02* (2006.01)
*G01D 18/00* (2006.01)
*G01N 21/27* (2006.01)
*G06Q 10/08* (2012.01)

(52) U.S. Cl.
CPC .......... *G01N 21/274* (2013.01); *G06Q 10/0875* (2013.01); *G06Q 10/087* (2013.01)
USPC ............... 705/29; 700/121; 705/28; 705/400; 702/85; 702/159; 702/199; 702/83

(58) Field of Classification Search
CPC .............. G05B 2219/45031; H01L 22/20; H01L 21/67276; G06Q 10/0875; G06Q 10/087
USPC ......... 700/121; 209/577; 705/400; 29/832, 29/840; 702/85, 159, 199, 83
See application file for complete search history.

(56) References Cited

U.S. PATENT DOCUMENTS

| 3,956,636 | A | * | 5/1976 | Williams | .................... | 250/559.4 |
| 4,020,950 | A | * | 5/1977 | Williams | ..................... | 209/588 |
| 4,276,983 | A | * | 7/1981 | Witmer | ......................... | 209/587 |
| 4,344,064 | A | * | 8/1982 | Bitler et al. | ..................... | 338/334 |
| 4,553,838 | A | * | 11/1985 | Madsen | ..................... | 356/237.1 |

(Continued)

FOREIGN PATENT DOCUMENTS

JP 05285458 A * 11/1993
JP 10291515 A * 11/1998

(Continued)

*Primary Examiner* — Olusegun Goyea
(74) *Attorney, Agent, or Firm* — Oliff & Berridge, PLC

(57) ABSTRACT

An efficient method of boxing fuel injectors with a good yield where a predetermined quality is secured in a predetermined number of fuel injectors forming a set for one engine, that is, a method of boxing fuel injectors, a first number of which are scheduled to be mounted in an engine, in a single box in a second number larger than the first number, provided with a step of measuring a characteristic value for the second number of fuel injectors, wherein when the first number of the characteristic values forms a set, the number of combinations of the characteristic values where a total value of this one set's worth of the characteristic values becomes a first management value or less when selecting one set's worth of the characteristic values from the second number of the characteristic values, is defined as the "number of good part combinations", and the number of possible combinations of one set's worth of the characteristic values is defined as the "number of possible combinations", the fuel injectors being boxed in a single box so that the number of the good part combinations becomes a rate of a fourth management value or more to the number of possible combinations.

5 Claims, 1 Drawing Sheet

(56) References Cited

U.S. PATENT DOCUMENTS

| | | | |
|---|---|---|---|
| 5,464,981 A * | 11/1995 | Squyres et al. | 250/341.8 |
| 5,471,311 A * | 11/1995 | van den Bergh et al. | 356/446 |
| 5,791,497 A * | 8/1998 | Campbell et al. | 209/577 |
| 5,954,206 A * | 9/1999 | Mallon et al. | 209/580 |
| 6,119,049 A * | 9/2000 | Peddle | 700/121 |
| 6,734,383 B1 * | 5/2004 | Calcoen et al. | 209/577 |
| RE39,016 E * | 3/2006 | Peddle | 700/121 |
| 7,483,477 B2 * | 1/2009 | Nygaard, Jr. | 375/224 |
| 2003/0033040 A1 * | 2/2003 | Billings | 700/97 |
| 2003/0222668 A1 * | 12/2003 | Hung et al. | 324/762 |
| 2004/0206046 A1 * | 10/2004 | Nakagawa et al. | 53/65 |
| 2005/0071101 A1 * | 3/2005 | Nishimura | 702/83 |
| 2007/0051670 A1 * | 3/2007 | Yunker et al. | 209/658 |
| 2007/0157994 A1 * | 7/2007 | Scoville et al. | 144/380 |
| 2008/0000547 A1 * | 1/2008 | Barker et al. | 144/329 |
| 2008/0000548 A1 * | 1/2008 | Liu et al. | 144/360 |
| 2009/0257646 A1 * | 10/2009 | Moon et al. | 382/149 |
| 2010/0017346 A1 * | 1/2010 | Extrand et al. | 705/400 |
| 2010/0096299 A1 * | 4/2010 | Adams et al. | 209/577 |

FOREIGN PATENT DOCUMENTS

| | | | |
|---|---|---|---|
| JP | 2000304822 A | * | 11/2000 |
| JP | 2001171022 A | * | 6/2001 |
| JP | A-2004-324510 | | 11/2004 |
| JP | A-2006-277217 | | 10/2006 |

* cited by examiner

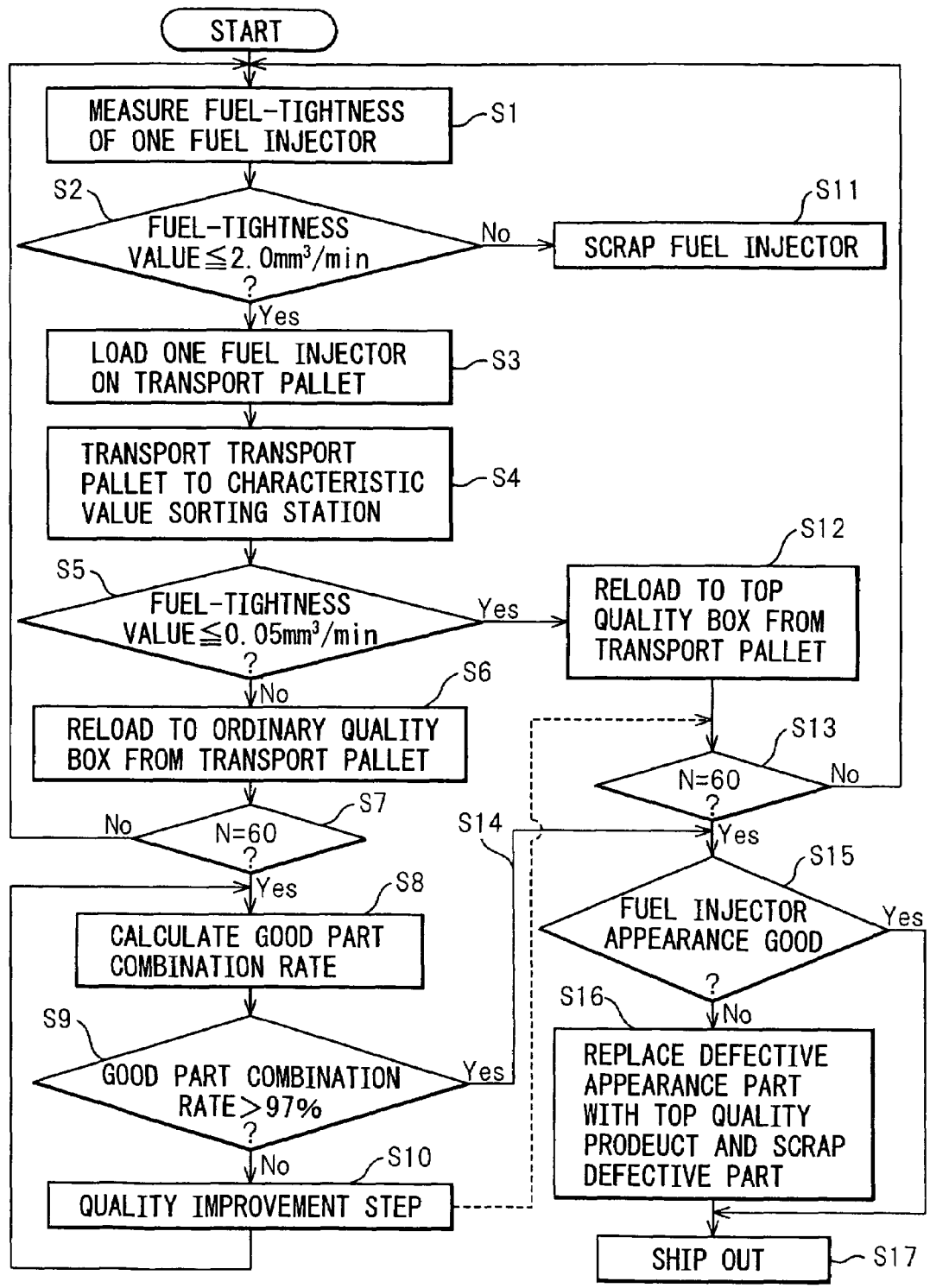

METHOD OF BOXING FUEL INJECTORS

BACKGROUND OF THE INVENTION

1. Field of the Invention

The present invention relates to a method of boxing fuel injectors for an engine. More particularly, the present invention relates to a method of preparing a box holding a large number of fuel injectors in which a predetermined quality is secured in a predetermined number of fuel injectors forming a set for one engine.

2. Description of the Related Art

A plurality of engine parts, in this case fuel injectors, are usually used for each final assembled part, that is, engine. This plurality will be called the "first number" and this plurality of fuel injectors will be called "a set of fuel injectors". In this case, the total value of the characteristic values of the fuel injectors forming a set sometimes has an effect on the performance of the engine.

Note that the "characteristic value" in the present specification means the performance or precision or other aspect of quality of a fuel injector. Further, the judgment as to a good part and defective part is usually made based on a management value (judgment value or threshold value) relating to the characteristic value.

As a characteristic value of a fuel injector, there is the amount of fuel leakage (fuel-tightness value). A fuel injector preferably has a fuel-tightness value of zero, but realistically a fuel injector can be used if the fuel-tightness value is slight. If the total of the fuel-tightness values of a set of fuel injectors is large, there is the danger that the lubrication oil in the engine will be diluted by the fuel and the engine bearings etc. will be damaged.

Note that in the past, the practice had been to inspect each of the fuel injectors scheduled to be mounted in an engine for that characteristic value and pack and ship out a predetermined number of only top quality parts in a single box. This "predetermined number" is a number roughly corresponding to several sets and is called a "second number".

In the case of this boxing management, the practice had been to employ only fuel injectors with particularly small fuel-tightness values (top quality) and to strictly manage them so that the management value was satisfied even in the worst combination, but there was the problem that fuel injectors with characteristic values usable for single parts were classified as defective parts and the yield therefore became poorer.

SUMMARY OF THE INVENTION

The present invention was made in consideration of the above problem and has as its object the provision of an efficient method of boxing fuel injectors with a good yield enabling a predetermined quality to be secured by a predetermined number of fuel injectors in a set for an engine.

The present invention provides a method of boxing as set forth in the claims of the claim section as means for achieving the above object.

According to a first aspect of the present invention, there is provided a method of boxing fuel injectors, a first number of which are scheduled to be mounted in an engine, in a box in a second number larger than the first number, provided with a step S1 of measuring a characteristic value for the second number of fuel injectors, wherein when the first number of the characteristic values forms a set, the number of combinations of the characteristic values where a total value of this set's worth of the characteristic values becomes a first management value or less when selecting one set's worth of the characteristic values from the second number of the characteristic values, is defined as the "number of good part combinations", and the number of possible combinations of one set's worth of the characteristic values is defined as the "number of possible combinations", the method boxes the fuel injectors in a box so that the number of the good part combinations becomes a ratio of a fourth management value or more to the number of possible combinations.

Due to this, it becomes possible to provide a method of boxing fuel injectors with a good yield able to secure a predetermined quality in a predetermined number of fuel injectors forming a set for an engine.

The idea is that when the probability of the total of the characteristic values for a set of fuel injectors taken out from a box storing a second number of injectors exceeding a management value (probability of being a defective part) is extremely low, the fuel injectors as a whole packed in this box are shipped out as passing parts. The value of the judgment criteria of a defective part for shipment of the boxed fuel injectors as a whole as passing parts is a value close to 0% and is determined by statistical methods.

According to a second aspect of the present invention, there is provided a method of boxing fuel injectors characterized in that a characteristic value sorting station is provided with a first quality box able to store the second number of fuel injectors and a second quality box able to store the second number of fuel injectors and by being provided with a step S5 of judging a fuel injector based on a third management value, a step S12 of storing that fuel injector in the first quality box if the characteristic value is the third management value or less, a third management value sorting step S6 of storing that fuel injector in the second quality box if the characteristic value is larger than the third management value, a computation step S8 of computing the characteristic values of the fuel injectors stored in the second quality box, the step computing a good part combination rate comprised of a ratio of the number of good part combinations with respect to the number of possible combinations, a good part combination rate judgment step S9 of comparing and judging the good part combination rate in the second quality box with a fourth management value, a passing part transport step S14 of transporting the second quality box as a passing part to a predetermined location at the shipment station side when the good part combination rate in the second quality box is larger than the fourth management value, and a quality improvement step S10 of taking out the third number of the fuel injectors of the second quality box from the second quality box, moving them to a predetermined location, taking out the same number of fuel injectors as the third number from the first quality box, and using these to replenish the second quality box when the good part combination rate in the second quality box is the fourth management value or less.

The first quality box stores fuel injectors of a top quality, while the second quality box stores fuel injectors of an ordinary quality. By sorting fuel injectors into the first quality box and second quality box, it becomes possible to minimize the number of times of repetition of the quality improvement step and greatly improve the production efficiency.

Further, at another inspection step in the downstream process (for example, inspection of the appearance), if a defective part occurs from the second quality box, this defective part is ejected and a top quality part from the first quality box is used to replenish the second quality box. Due to this, it is no longer necessary to recalculate the good part combination rate of the second quality box. Note that this recalculation time is about 10 minutes and becomes a major factor obstructing the production efficiency.

According to a third aspect of the present invention, the method of boxing fuel injectors is characterized in that, in the quality improvement step S10, when the third number of the fuel injectors of the second quality box are taken out from the second quality box, the third number of the fuel injectors are taken out in order from the largest characteristic value. Due to this, it becomes possible to clear the good part combination rate by a small number of repetitions of the quality improvement step.

According to a fourth aspect of the present invention, the method of boxing fuel injectors is characterized in that, in the quality improvement step S10, the predetermined location is the first quality box. Due to this, it becomes possible to ship out parts without scrapping the fuel injectors taken out from the second quality box and to reduce the costs.

According to a fifth aspect of the present invention, the method of boxing fuel injectors is characterized by, in the recomputation step S8, fixing all of the characteristic values of the third number of fuel injectors stored from the first quality box to the second quality box at the third management value to compute the good part combination rate. Due to this, it is no longer necessary to recalculate the good part combination rate of the second quality box.

According to a sixth aspect of the present invention, the method of boxing fuel injectors is characterized by being further provided with an appearance inspection step S15 for inspecting the outer appearance after the passing part transport step S14.

According to a seventh aspect of the present invention, the method of boxing fuel injectors is characterized in that the characteristic value is a fuel-tightness value.

Note that the reference notations after the steps show the correspondence with specific steps described in the following embodiment.

BRIEF DESCRIPTION OF THE DRAWINGS

These and other objects and features of the present invention will become clearer from the following description of the preferred embodiments given with reference to the attached drawing, wherein FIG. 1 is a flow chart showing the steps of the method of boxing fuel injectors of the present invention.

DESCRIPTION OF THE PREFERRED EMBODIMENT

Below, a preferred embodiment of the present invention will be explained with reference to the drawing. FIG. 1 is a flow chart showing the steps of the method of boxing fuel injectors of the present invention.

First, referring to FIG. 1, the steps of the method of boxing fuel injectors according to the embodiment of the present invention will be explained. FIG. 1 shows the steps for packing 60 fuel injectors for 8-cylinder engines as a lot in a box. That is, the first number is "8", while the second number is "60".

First, at step 1, each fuel injector is measured for fuel tightness. At step 2, the level of the fuel-tightness value of a fuel injector is judged using 2.0 mm$^3$/min (second management value) as a criteria. Step 2 is called the "second management value judgment step". When the fuel-tightness value is larger than 2.0 mm$^3$/min, the fuel injector is discarded as a defective part (step 11).

When the fuel-tightness value is 2.0 mm$^3$/min or less, the fuel injector is placed on a transport pallet with an ID tag as a passing part (step 3). At this time, the measured fuel-tightness value is read into the ID tag of the transport pallet. The transport pallet carrying the fuel injector is transported placed on a conveyor line and reaches a characteristic value sorting station (step 4).

The characteristic value sorting station is provided with two types of boxes, that is, a top quality box (first quality box) able to store 60 (second number) fuel injectors and an ordinary part box (second quality box) able to store 60 fuel injectors. Further, the fuel-tightness value of the transported fuel injector is read from the data of the ID tag attached to the transport pallet by a wireless reading means. Next, it is judged if the fuel injector is a top quality part or an ordinary part based on a fuel-tightness value of 0.05 mm$^3$/min (third management value) (step 5).

If that fuel-tightness value is 0.05 mm$^3$/min or less, that fuel injector is detached from the transport pallet and stored in the top quality box (step 12), while if that fuel-tightness value is larger than 0.05 mm$^3$/min, that fuel injector is detached from the transport pallet and stored in the ordinary part box (step 6). At that time, the fuel-tightness value data read by the reading means is transmitted by a wireless transmitting means and read into an ID tag attached to the box in which the fuel injector is stored (top quality box or ordinary part box) (steps 6 and 12).

Next, the flow of the steps relating to the ordinary part box will be explained. After step 6, at step 7, the number N of fuel injectors stored in the ordinary part box is counted by a counting means and it is judged if the number N of fuel injectors is 60 or not. If the number N of fuel injectors is less than 60, the routine returns to right before step 1. Further, the steps from step 1 to step 7 are repeated until the number N of fuel injectors reaches 60.

When the number N of fuel injectors stored in the ordinary part box reaches 60, the routine proceeds to step 8. At step 8, any eight data are selected from the 60 fuel-tightness value data and this eight data are totaled up. Note that this eight data is called "a set of data". There are a possible $_{60}C_8$ combinations of eight data selected from the 60 fuel-tightness value data. $_{60}C_8$ combinations equal about 2.6 billion combinations. Computation for totaling the approximately 2.6 billion fuel-tightness values would require about 10 minutes.

On the other hand, 5.0 mm$^3$/min or less is the total fuel-tightness value of a set of fuel injectors (8) not having a detrimental effect on the engine. The combination of a set satisfying this total fuel-tightness value is called a "good part combination". Further, a combination where the total fuel-tightness value of a set of fuel injectors (8) is larger than 5.0 mm$^3$/min is called a "defective part combination". That is, the number of combinations of fuel injectors where the total value of the fuel-tightness values becomes 5.0 mm$^3$/min or less divided by $_{60}C_8$ becomes the good part combination rate. Further, the number of combinations of fuel injectors where the total value of the fuel-tightness values becomes larger than 5.0 mm$^3$/min divided by $_{60}C_8$ becomes the defective part combination rate. At step 8, this good part combination rate is calculated.

Next, at step 9, it is judged if this good part combination rate is larger than 97% (fourth management value) in the ordinary part box. Step 9 is called the "good part combination rate judgment step". If the good part combination rate is larger than 97%, the ordinary part box is transported as a passing part to the appearance inspection station (step 14). If the good part combination rate is 97% or less, the ordinary part box is a failed part and the routine proceeds to step 10.

At this step 8, the defective part combination rate is calculated. At step 9, this defective part combination rate and the judgment criteria value of 3% are compared. Based on the results of this judgment, the routine proceeds to step 10 or step 14.

At step 10, one fuel injector in the ordinary part box is taken out. As a replacement, one fuel injector in the top quality box is taken from the top quality box and stored in the ordinary part box. The fuel injector taken out from the ordinary part box is in principle stored in the top quality box, but may also be scrapped. Step 10 is called the "quality improvement step".

The fuel-tightness value data of the one top quality part fuel injector stored in the ordinary part box as a replacement, not the actual fuel-tightness value, but the data rounded up and fixed to 0.05 $mm^3$/min, is read into the ID tag of the ordinary part box. Due to this, when a defective part is discovered in the later separate inspection (for example, inspection of appearance) and this defective part is replaced with a top quality part, it becomes possible to omit the calculation of combinations. Details of this will be explained later.

After step 10 is completed, the routine returns to just before step 8, where the calculation of the combination rate of step 8 is executed again. Further, step 8 to step 10 are repeated until the good part combination rate becomes larger than 97% or until the defective part combination rate becomes 3% or less. At the time of this repetition, only naturally, the fuel injector taken out from the ordinary part box is not an already stored top quality part, but a stored remaining ordinary part. In this repeated quality improvement step 10, when taking out fuel injectors of the ordinary part box, the fuel injectors can also be taken out in the order from the largest fuel-tightness value. Due to this, it is possible to reduce the number of repetitions of the quality improvement step 10.

Further, at the initial quality improvement step 10, it is also possible not to take out only one fuel injector of the ordinary parts, but to take out for example three (third number) and replace them with the top quality parts. Due to this, statistically the probability of the quality improvement step 10 being able to be finished by a single operation becomes higher. Only naturally, it is also possible to select these three in the order from the largest fuel-tightness value.

In this way, by sorting fuel injectors into a top quality box and ordinary part box, the process of the quality improvement step S10 becomes simpler and clearer, the number of repetitions of the quality improvement step S10 can be minimized, and the production efficiency can be greatly improved.

The ordinary part box transported to the appearance inspection station at step 14 is visually inspected for the appearance of its 60 fuel injectors at step 15. If any parts defective in appearance are found, these defective appearance parts are scrapped. The same number of top quality parts as the defective appearance parts are taken out of the top quality box and stored in the ordinary part box. If the appearances of the top quality parts stored in this ordinary part box pass, at step 17, this ordinary part box is recognized as a final passing part and transported to the shipment station where it is shipped out. Further, when no defective appearance parts can be discovered at step 15, the box is immediately transported to the shipment station at step 17.

At step 10, the fuel-tightness values of the top quality part fuel injectors are all rounded up and fixed at the worst value of the fuel-tightness values of the top quality parts, that is, 0.05 $mm^3$/min (third management value), so the fuel-tightness values of the defective appearance parts should always be the third management value or more (worse fuel-tightness value). For this reason, the good part combination rate including the top quality parts exchanged with the defective appearance parts cannot become worse than the good part combination rate of the ordinary part box before the exchange. For this reason, it becomes possible to ship out the ordinary part box without recalculating the new combination rate including top quality parts exchanged with the defective appearance parts.

Next, the flow of the process relating to the top quality box will be explained from step 12. At step 12, a fuel injector judged as a top quality part at step 5 is stored in the top quality box. Further, the top quality box also stores ordinary part fuel injectors taken out from the ordinary part box and moved to it at step 10. That is, the fuel injectors in the top quality box are of two types: the case of all top quality parts and the case of top quality parts and ordinary parts mixed together. Whatever the case, at step 13, the number N of fuel injectors in the top quality box is counted. Further, when the number N of fuel injectors in the top quality box is less than 60, the process flow returns to just before step 1. During this time, the top quality box stops at the characteristic value sorting station.

Further, when the fuel injectors in the top quality box reach 60, the top quality box moves to the appearance inspection station of step 15. Further, the appearance inspection step of step 15 is executed. The steps after that are the same in content as the steps explained for the ordinary part box. After that, the top quality box is also shipped out.

Here, a specific example of the first, second, and third numbers; the first, second, third, and fourth management values; and the first and second quality boxes in the first embodiment is given below:

First number: 8
Second number: 60
Third number: 3
First management value: 5.0 $mm^3$/min
Second management value: 2.0 $mm^3$/min
Third management value: 0.05 $mm^3$/min
Fourth management value: 97%
First quality box: Top quality box
Second quality box: Ordinary part box Note that engine may be a gasoline engine, a diesel engine, or another type. The fuel injector may be a direct injection type, a port injection type, an intake pipe injection type, or another type. The characteristic value is not limited to the fuel-tightness value and may the injection port area or any other one which has an effect on the performance or precision of the fuel injectors.

Due to the above, it becomes possible to provide an efficient method of boxing fuel injectors with a good yield enabling a predetermined quality to be secured in a predetermined number of fuel injectors forming a set for an engine.

While the invention has been described with reference to specific embodiments chosen for purpose of illustration, it should be apparent that numerous modifications could be made thereto by those skilled in the art without departing from the basic concept and scope of the invention.

The invention claimed is:

1. A method of boxing fuel injectors, a first number of which are scheduled to be mounted in an engine, in a box in a second number larger than the first number, each fuel injector has a characteristic value, wherein when the first number of the characteristic values forms a set, the number of combinations of the characteristic values where a total value of the one set's worth of the characteristic values becomes a first management value or less when selecting the one set's worth of the characteristic values from the second number of the characteristic values, is defined as the "number of good part combinations," and the number of possible combinations of the one set's worth of the characteristic values is defined as the "number of possible combinations," the method boxes the fuel injectors in a box so that the number of the good part combinations becomes a ratio of a fourth management value or more to the number of possible combinations, the method comprising:

a step of measuring the characteristic value for the second number of fuel injectors;

a second management value judgment step of judging the characteristic value of each fuel injector based on second management value, the step scrapping the fuel injector as a defective part if the characteristic value of the fuel injector is larger than the second management value and concluding that the fuel injector is a passing part if the characteristic value is the second management value or less;

a step of loading the passing part fuel injector on a transport pallet;

a step of transporting the passing part fuel injector to a characteristic value sorting station, the characteristic value sorting station being provided with a first quality box able to store the second number of the fuel injectors and a second quality box able to store the second number of the fuel injectors;

a step of judging the characteristic value of the fuel injector transported to the characteristic value sorting station based on a third management value;

a step of storing the fuel injector in the first quality box if the characteristic value is equal to the third management value or less;

a third management value sorting step of storing the fuel injector in the second quality box if the characteristic value is larger than the third management value;

a step of judging if the fuel injectors stored in the second quality box have reached the second number;

a computation step of computing the characteristic values of the fuel injectors stored in the second quality box, the step computing a good part combination rate comprised of a ratio of the number of good part combinations with respect to the number of possible combinations;

a good part combination rate judgment step of comparing and judging the good part combination rate in the second quality box with the fourth management value;

a passing part transport step of transporting the second quality box as a passing part to a predetermined location at a shipment station side when the good part combination rate in the second quality box is larger than the fourth management value;

a quality improvement step of taking out a third number of the fuel injectors of the second quality box from the second quality box, moving them to a predetermined location, taking out the same number of fuel injectors as the third number from the first quality box, and using these to replenish the second quality box when the good part combination rate in the second quality box is the fourth management value or less; and a recomputation step of recomputing the good part combination rate of the second quality box after the quality improvement step;

wherein the characteristic value is a fuel-tightness value.

2. The method as set forth in claim 1, wherein in the quality improvement step, when the thid number of the fuel injectors of the second quality box are taken out from the second quality box, the third number are taken out from the fuel injector in order from the largest characteristic value.

3. The method as set forth in claim 1, wherein in the quality improvement step, the predetermined location is the first quality box.

4. The method as set forth in claim 1, wherein in the recomputation step, the characteristic values of the third number of fuel injectors stored from the first quality box to the second quality box are all fixed to a third management value for computation of the good part combination rate.

5. The method as set forth in claim 4, further provided with an appearance inspection step for inspecting the outside appearance after the passing part transport step.

* * * * *